US011185250B2

(12) United States Patent
Windheuser et al.

(10) Patent No.: US 11,185,250 B2
(45) Date of Patent: Nov. 30, 2021

(54) MEDICAL DEVICES AND RELATED METHODS OF USE

(71) Applicant: Boston Scientific Scimed, Inc., Maple Grove, MN (US)

(72) Inventors: Kevin Windheuser, Hopkinton, MA (US); Shawn Ryan, Littleton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 846 days.

(21) Appl. No.: 15/399,176

(22) Filed: Jan. 5, 2017

(65) Prior Publication Data

US 2017/0224249 A1    Aug. 10, 2017

Related U.S. Application Data

(60) Provisional application No. 62/291,787, filed on Feb. 5, 2016.

(51) Int. Cl.
| | |
|---|---|
| *A61B 5/06* | (2006.01) |
| *A61M 5/14* | (2006.01) |
| *A61B 8/08* | (2006.01) |
| *A61B 5/00* | (2006.01) |
| *A61B 5/11* | (2006.01) |

(52) U.S. Cl.
CPC .............. *A61B 5/061* (2013.01); *A61B 5/065* (2013.01); *A61B 5/687* (2013.01); *A61B 5/6847* (2013.01); *A61B 8/0841* (2013.01); *A61B 8/481* (2013.01); *A61M 5/14* (2013.01); *A61B 5/11* (2013.01); *A61M 2210/105* (2013.01)

(58) Field of Classification Search
CPC ........... A61B 5/06; A61B 5/061; A61B 5/064; A61B 5/065; A61B 5/68; A61B 5/6846; A61B 5/6848; A61B 5/687; A61B 5/6876; A61B 8/0833; A61B 8/0841; A61B 8/48; A61B 8/481
USPC ....... 600/424–427, 431, 437, 495, 462, 463, 600/459; 606/7, 13–16; 604/19–21; 128/898
See application file for complete search history.

(56) References Cited

U.S. PATENT DOCUMENTS

| | | | | |
|---|---|---|---|---|
| 5,746,736 A | * | 5/1998 | Tankovich | A61B 18/0218 606/10 |
| 5,836,940 A | * | 11/1998 | Gregory | A61B 18/245 606/15 |
| 6,117,128 A | * | 9/2000 | Gregory | A61B 18/24 606/15 |
| 7,549,424 B2 | * | 6/2009 | Desai | A61B 8/0841 128/898 |
| 8,926,494 B1 | | 1/2015 | Cook et al. | |
| 2004/0221853 A1 | * | 11/2004 | Miller | A61M 16/0486 128/207.14 |
| 2007/0197954 A1 | | 8/2007 | Keenan | |
| 2009/0131790 A1 | | 5/2009 | Munrow et al. | |

(Continued)

*Primary Examiner* — Ahmed M Farah
(74) *Attorney, Agent, or Firm* — Bookoff McAndrews, PLLC

(57) ABSTRACT

The present disclosure is directed to a method of determining a position of a medical instrument. The method may include inserting a first material into a body and adjacent to the medical instrument, analyzing at least one characteristic of the inserted first material, and determining the position of the medical instrument based on the analysis of the at least one characteristic.

16 Claims, 4 Drawing Sheets

(56) References Cited

U.S. PATENT DOCUMENTS

| | | | |
|---|---|---|---|
| 2010/0016729 A1* | 1/2010 | Futrell | A61B 5/0086 600/473 |
| 2010/0291521 A1* | 11/2010 | Simon | A61B 5/06 434/262 |
| 2011/0112511 A1 | 5/2011 | Singer | |
| 2012/0226101 A1* | 9/2012 | Tinkham | A61B 1/00066 600/106 |
| 2012/0271204 A1* | 10/2012 | Peyman | A61B 5/1455 601/2 |
| 2014/0288412 A1* | 9/2014 | Schwartz | A61B 34/20 600/424 |
| 2014/0316269 A1* | 10/2014 | Zhang | A61N 7/02 600/439 |
| 2016/0183804 A1* | 6/2016 | Kowalewski | A61B 5/0084 600/425 |

\* cited by examiner

MEDICAL DEVICES AND RELATED METHODS OF USE

CROSS-REFERENCE TO RELATED APPLICATIONS

This application claims the benefits of priority from U.S. Provisional Application No. 62/291,787, filed on Feb. 5, 2016, the entirety of which is incorporated herein by reference.

TECHNICAL FIELD

Embodiments of the present disclosure relate generally to medical devices and methods of using such devices. More particularly, embodiments of the disclosure relate to medical devices and methods for use in medical applications, such as, for example, determining whether a tool is positioned correctly within a patient.

BACKGROUND OF THE DISCLOSURE

Many medical procedures involve precise positioning of medical devices within a patient's body. Often the target area within the body or the tools used for the medical procedure are difficult to visualize, making it difficult to determine correct placement. For example, one treatment of Gastroesophageal Reflux Disease (GERD) may include such precise placement and its confirmation. This treatment includes injecting a liquid solution (e.g., a bulking agent) into the Lower Esophageal Sphincter (LES). Once injected into the LES, the liquid solution expands the muscle permanently, thus treating GERD. In some examples, however, a physician may encounter a lack of visibility of the needle once it enters the LES. The needle tip can be incorrectly placed and enter undesired areas of the body, e.g., the patient's aorta. If the fluid enters the aorta, which is adjacent to the esophagus, complications can occur.

As such, there exists a need for a device that improves tool, e.g., needle, placement and visibility.

SUMMARY OF THE DISCLOSURE

Aspects of the present disclosure relate to, among other things, confirming correct placement of a medical instrument. Each of the aspects disclosed herein may include one or more of the features described in connection with any of the other disclosed aspects.

In one example, a method of determining a position of a medical instrument may include inserting a first material into a body and adjacent to the medical instrument, analyzing at least one characteristic of the inserted first material, and determining the position of whether the medical instrument based on the analysis of the at least one characteristic.

Examples of the method of determining a position of a medical instrument may additionally and/or alternatively include one or more other features. For example, the least one characteristic may be at least one of movement, density, chemical composition, and reflectivity. The first material may include a reflective material. The reflective material may be at least one of zinc, aluminum, gold, silver, platinum, and gas bubbles. The method may include performing a medical procedure. The medical procedure may include injecting a second material. The second material may be a bulking agent.

In another example, a method of performing a medical procedure may include inserting a medical instrument into a body, inserting the medical instrument into tissue of the body, injecting a flowable first material adjacent to the medical instrument, analyzing movement of the first material to determine a position of the medical instrument, and performing the medical procedure.

Examples of the method of performing a medical procedure may additionally and/or alternatively include one or more other features. For example, the medical instrument may be inserted into the digestive tract. The step of analyzing movement may include determining whether the movement of the first material after injection is below a threshold of movement. The performed medical procedure may include injecting a second material into the patient. The second material may be a bulking agent. The medical instrument may be a needle. The tissue may be in the esophagus.

In another example, a method of determining a position of a tip of a needle may include injecting a reflective material through the needle and into the body adjacent to the tip of the needle, and analyzing movement of the reflective material to determine the position of the tip of the needle.

Examples of the method of determining a position of a tip of a needle may additionally and/or alternatively include one or more other features. For example, the reflective material may include at least one of zinc, aluminum, gold, silver, platinum, and gas bubbles. The method may include inserting the tip of the needle into an esophagus. The position of the tip of the needle may be within a Lower Esophageal Sphincter. The method may include injecting a bulking agent into the Lower Esophageal Sphincter. The method may include repositioning the tip of the needle if the movement of the reflective material is above a threshold.

It is to be understood that both the foregoing general description and the following detailed description are exemplary and explanatory only and are not restrictive of the scope of disclosed aspects, as set forth by the claims.

BRIEF DESCRIPTION OF THE DRAWINGS

The accompanying drawings, which are incorporated in and constitute a part of this specification, illustrate embodiments of the disclosure and together with the description, serve to explain the principles of the disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a patient. The term "proximal" refers to the end closest to the user when placing the device into the patient. When used herein, the terms "approximately" and "substantially" may indicate a range of values within +/−5% of a stated value.

Aspects of the present disclosure relate to systems and methods for confirming a medical device is positioned at a correct, desired location, e.g., target area. For example, a medical device, such as a therapeutic or diagnostic tool, may be inserted into a patient. An operator may position the tool, and particularly an operative tool portion such as a tip, to a location the operator believes is within the target area. The operator may then inject a first material (e.g., a reflective material) into the patient. The operator or a processor may analyze the first material in the patient to determine if the tool is at the desired location, e.g., the target area. For example, an operator may analyze any suitable characteristic to determine if the tool is correctly placed, including, for example, movement of the first material, flow of the first material, dissipation/concentration of the first material and/or strength of reflection.

The examples described in this disclosure focus on accessing and positioning a tool within the gastrointestinal tract and injecting material into the LES, but the system and methods described herein are not limited thereto. For example, the devices and methods described herein may be used in the urinary tract, pulmonary tract, and/or another lumen, organ, or tissue in the body where correct placement of a tool is desired.

Figure 1:
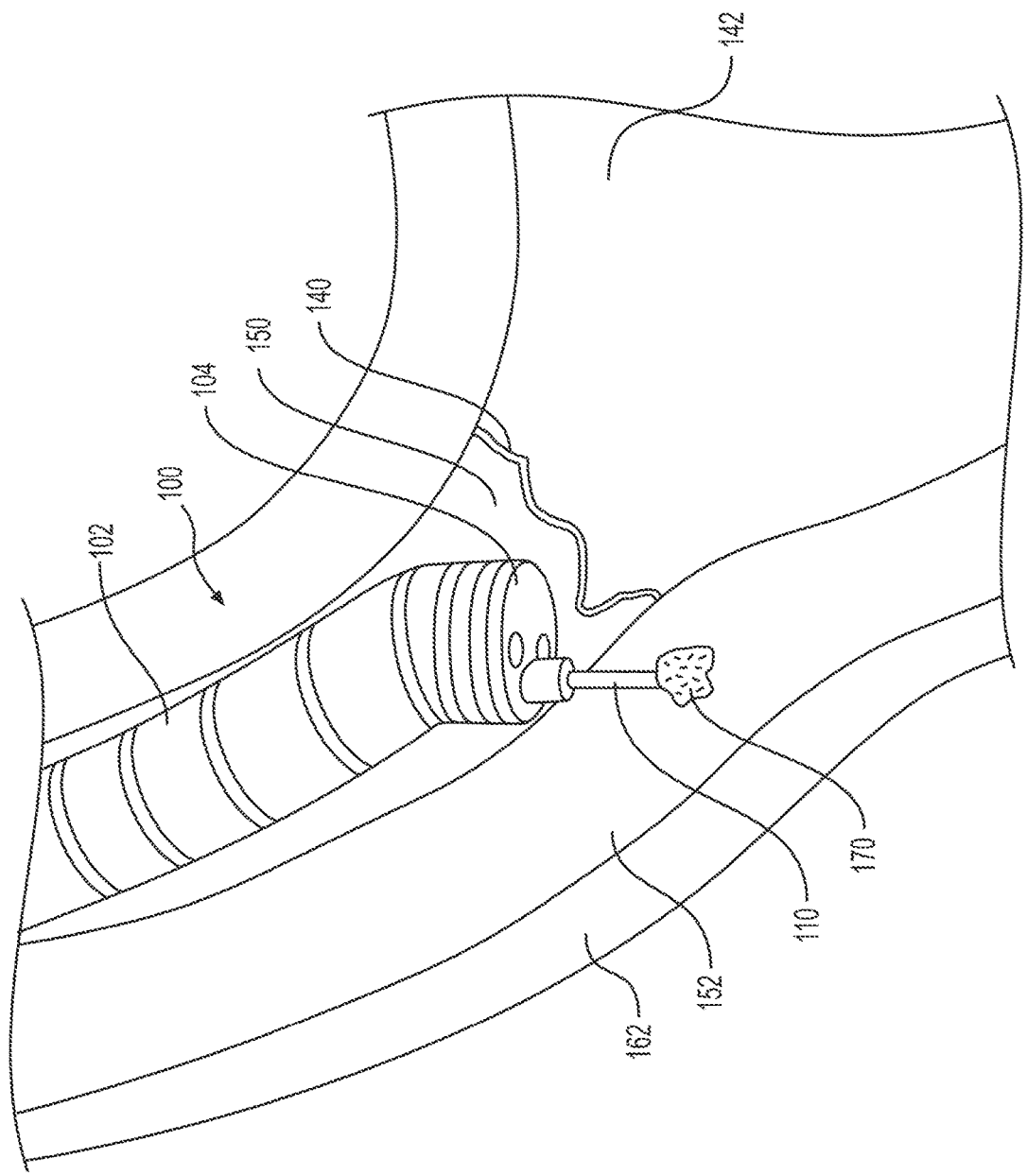
FIG. 1 illustrates an exemplary delivery device including a tool injecting material into a patient's LES.

FIG. 1 depicts medical device 100. Medical device 100 may include a delivery device 102 (e.g., an endoscope, sheath, catheter, etc.). Delivery device 102 may position within a patient body medical devices or tools (e.g., tool 110) for performing a medical procedure, e.g., injecting material. Delivery device 102 may be used for procedures within or adjacent to various body organs, such as, an esophagus, a heart, a stomach, a pelvic area, a bladder, an intestine, or any other portion of a gastrointestinal, urinary, or pulmonary tract. Delivery device 102 may be configured for insertion into a patient's body through a natural, anatomical opening or through an incision performed by a surgeon. In some embodiments, delivery device 102 may be used in natural orifice transluminal endoscopic surgery (NOTES) procedures or single incision laparoscopic surgical (SILS) procedures. Accordingly, delivery device 102 may be shaped and sized for placement into a patient via a body cavity or an incision.

Delivery device 102 includes a proximal end (not shown) and a distal end 104. Delivery device 102 may include one or more working channel(s) (e.g., a single working channel or multiple channels as shown in FIG. 1) extending substantially longitudinally (axially) between the proximal end and the distal end 104 of delivery device 102. The one or more working channels may have any suitable size, cross-sectional area, shape, and/or configuration to, for example, introduce medical devices (e.g., tool 110) to distal end 104 of delivery device 102. In some embodiments, the working channel(s) may be made of, or coated with, a polymeric or lubricious material to enable the introduced medical devices to pass through the working channel(s) with ease.

Delivery device 102 may be a flexible tube, made from any suitable biocompatible material known to one of ordinary skill in the art and having sufficient flexibility to traverse tortuous anatomy. Such materials may include, but are not limited to, rubber, silicon, synthetic plastic, stainless steel, metal-polymer composites, and metal alloys of nickel, titanium, copper cobalt, vanadium, chromium, and iron. In some examples, the material forming delivery device 102 may be a superelastic material such as nitinol, which is a nickel-titanium alloy. In some examples, delivery device 102 may include layers of different materials and reinforcements. Delivery device 102 may have any cross-sectional shape and/or configuration and may be any desired dimension that can be received in a body cavity. In some examples, delivery device 102 may be made of, or coated with, a polymeric or lubricious material to enable delivery device 102 to pass through a body cavity with ease. Additionally, delivery device 102 may be steerable and may have areas of different flexibility or stiffness to promote steerability within the body cavity. Delivery device 202 of FIG. 3 may include any of the features and/or components of delivery device 102.

Medical tool 110 may be slidably inserted and advanced through one of the working channel(s) of delivery device 102. Medical tool 110 may be configured for use during a surgical method and/or diagnostic/therapeutic procedures. Tool 110 may be any device capable of injecting material, such as, for example, a needle for injecting a bulking agent into the LES. Tool 110, however, can be any therapeutic or diagnostic device that is used in a medical procedure in which its precise positioning is desirable.

FIG. 1 further depicts the aorta 162 and various aspects of the digestive tract, including esophagus 150, squamo-columnar junction 140, LES 152, and stomach 142. As mentioned above, however, the medical device and methods described herein may be used within any body tissue, body wall, and/or anatomical lumen.

Figure 4:
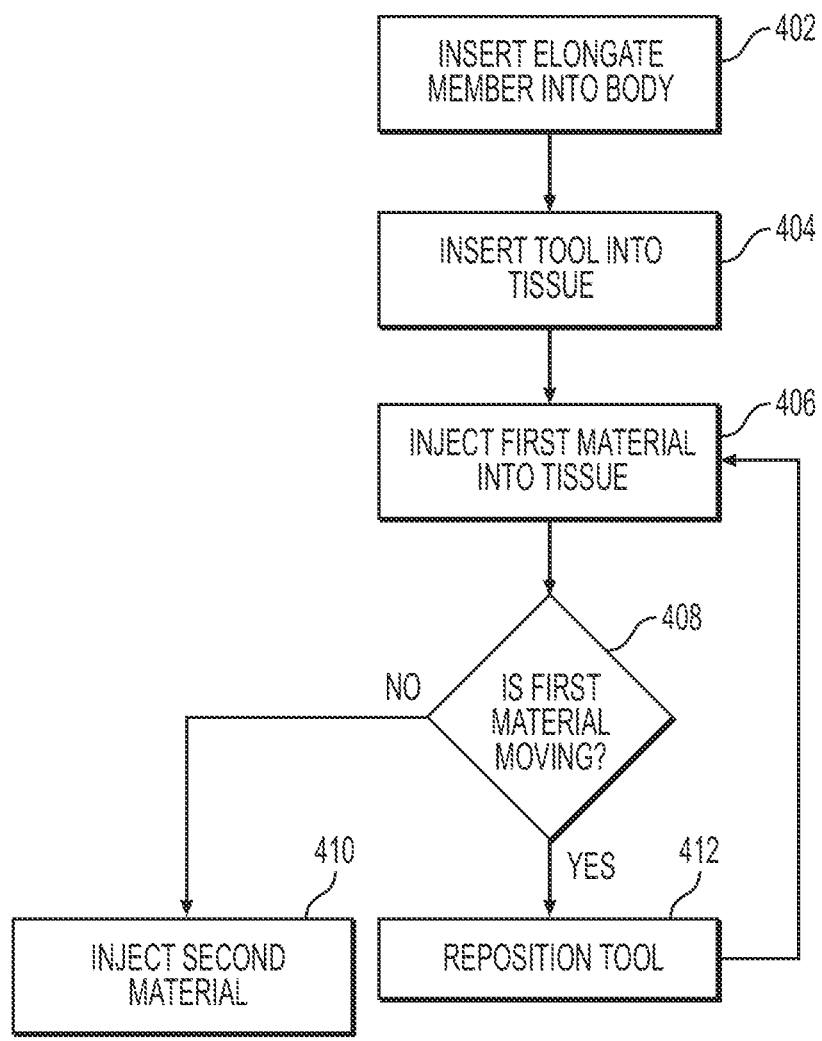
FIG. 4 is a block diagram of an exemplary method of using the medical devices disclosed herein.

FIG. 4 illustrates an exemplary method of use of a medical device (such as the medical device 100 of FIGS. 1 and 2) for determining/confirming correct placement of a tool, e.g., tool 110. For purposes of discussion, method 400 will be described using medical device 100 of FIGS. 1 and 2, as described above, but method 400 is not intended to be limited thereto. As shown in FIG. 4, method 400 includes steps 402, 404, 406, 408, 410, and 412. However, it should be noted that method 400 may include more or fewer steps as desired for a particular implementation and the order of the steps may be varied.

Method 400 may commence when an operator (e.g., a doctor or other medical personnel) inserts an elongate member (delivery device 102, for example) into a patient (step 402). The operator may position the distal end 104 of delivery 102 proximate a target area. A target area may be a site where the operator desires a medical instrument and/or tool to be positioned. For example, as shown in FIG. 1, delivery device 102 may be inserted through the patient's esophagus 150 until distal end 104 of delivery device 102 is proximate squamo-columnar junction 140. In some examples, an imaging device (e.g., separate from or associated with the elongate member) may be utilized to assist the operator in determining the desired position of distal end 104, as known in the art.

Figure 2:
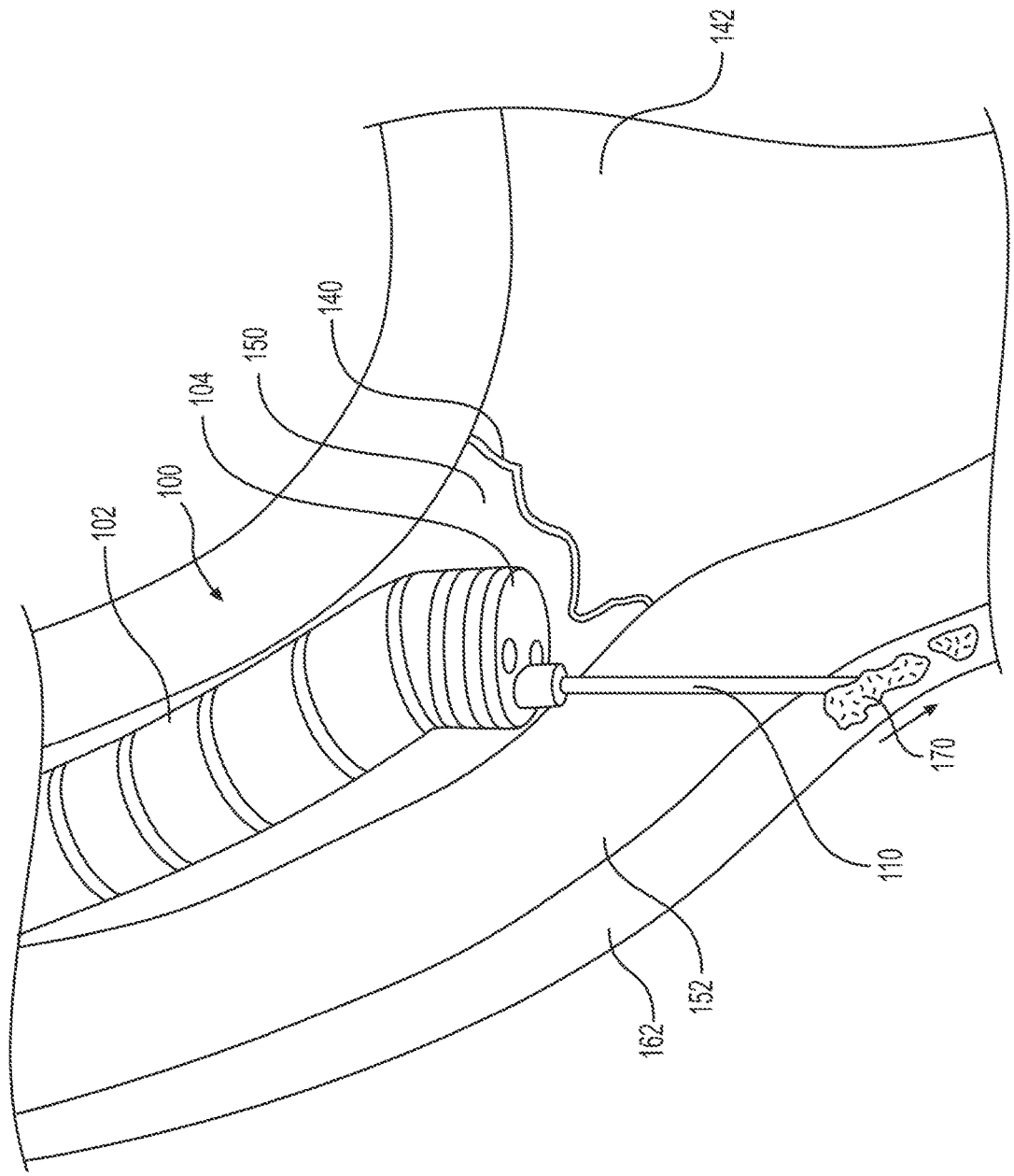
FIG. 2 illustrates the exemplary delivery device of FIG. 1 including the tool injecting material into the patient's aorta.

The elongate member/delivery device 102 may be adjusted so that a distal face of distal end 104 may be aimed at the target area. For example, as shown in FIGS. 1 and 2, delivery device 102 is curved or articulated toward a body wall (e.g., LES 152), so that the distal face of distal end 104 points toward the body wall. A medical device (e.g., tool 110) may be disposed within a working channel of delivery device 102, and a distal opening of that working channel may be positioned proximate to the target area (e.g., LES 152). In some examples, a tool is disposed within the delivery device during step 402. In other examples, the tool may be only partially disposed within the delivery device or may be external to the delivery device during step 402. The tool may then extend through the delivery device 102 to distal end 104 once the delivery device 102 is in the operator's desired position.

The operator may then move the tool until the operator believes the appropriate portion of the tool is in the desired position of the target area. For example, in step 404, an operator may insert a medical tool into tissue of the patient (e.g., the target tissue of a body wall that an operator desires the tool to be positioned within). In the example illustrated in FIG. 1, tool 110 (e.g., a needle) may be inserted into the LES 152, and specifically the tip of the needle is inserted within the target area.

Once the operator believes the tool is in the desired position, e.g., the target area, method 400 may then proceed to step 406. In step 406, the operator may inject a first material (e.g., a fluid) through the tool. In some examples, the first material may be a fluid that flows. The first material may be a water or saline solution with reflective, biocompatible particles. Such particles may include any material that is safe in the patient's body. For example, if the first material is injected into the wrong spot, the patient would experience no harm, and the physician could re-position the needle. In some examples, the first material may be a water or saline solution with nanoparticles like small air or other gas bubbles. These bubbles may be reflective. In some examples, the reflective particles may be include zinc, aluminum, silver, gold, platinum, or a combination thereof. As examples, zinc particles would reflect approximately 81% of energy (e.g., ultrasound energy), aluminum particles would reflect approximately 69%, silver would reflect approximately 85%, gold would reflect approximately 91%, and platinum would reflect approximately 93%. The reflected energy may provide the operator with an image of the first material including an image showing whether the first material is stationary or moving. With such information, an operator may infer where a second material (e.g., a bulking material) would go if injected through the current placement of tool 110.

Alternatively, a hypo-echoic fluid may be injected if the surrounding tissue is highly reflective. In this example, particles may be eliminated or unnecessary and saline may be the pre-injection.

Once injected, the first material may be analyzed within the patient. An operator, processor(s), or a combination thereof may analyze the first material once injected. An analyzed characteristic of the injected first material may indicate whether the tool is in the desired position. Any suitable characteristic may be analyzed and/or used to determine correct placement including, flow of a fluid, movement or lack of movement of particles (including direction and/or velocity), concentration of particles, strength of reflectivity, chemical make-up/reactions, etc. In one example, step 408 of method 400 may include determining whether the first material moved after injection.

By analyzing the injected first material, whether the tool is correctly placed may be determined. If the tool is determined to be at the correct, desired location, the operator may continue with the desired procedure (e.g., dissection, injecting a second material, etc.). If the analysis of the injected first material indicates that the tool is not in the correct position, the operator may reposition the tool, until the operator confirms it is in the correct position, and method 400 then may proceed to step 410.

In the example illustrated in FIG. 1, once the operator inserts tool 110 (e.g., a needle) into the LES and believes the injecting tip is within the desired target area (e.g., the tip of the needle is in the LES), the operator may inject the first material with reflective particles (e.g., a saline solution with zinc). A device used to image the reflective particles (e.g., an x-ray machine, an ultrasound, a transducer, etc.) may be used to image the injected first material. For example, an ultrasound device may be used on the exterior of the patient to image the interior of the esophagus 150, delivery device 102, tool 110, and/or first material 170. An operator or processor(s) may then determine if the injected material is moving (step 408). If the zinc-saline suspension is in the LES (e.g., tool 110 is correctly position), the suspension will not move on the ultrasound and the operator can be confident that the needle is in the correct, desired location to inject a second material (e.g., the active injection). Thus, in such an example, if the first material is not moving (step 408:No) or movement is below a certain threshold, method 400 may proceed to step 410 and the second material may be injected. An injected second material may be an active material (e.g., the purpose of the therapeutic or diagnostic procedure). In the example in which the operator is treating GERD, the second material may be a bulking agent.

If the tool (e.g., needle) went past the LES (e.g., into aorta 162) and then injected first material 170, first material 170 (e.g., the zinc-saline suspension) may move in the ultrasound image(s) as the suspension travels through the aorta 162 (as shown in FIG. 2). Thus, in such an example, if the first material 170 is moving at all or above threshold amount (step 408:Yes), method 400 may proceed to step 412, and the tool may be repositioned. For example, if the injecting tip of needle is positioned in aorta 162, the needle tip may be pulled toward distal end 104 of delivery device 102. Once the tool is repositioned (e.g., by the operator or a processor), method 400 may return to step 406 and inject the first material in the new, adjusted position.

Once the desired procedure is complete (e.g., tool 110 injects a bulking agent into the LES 152), the delivery device may be removed from the patient.

In some examples, step 404 may not be performed. An operator, for example, may desire the tool (e.g., any tool capable of dispensing fluid) to be positioned into a lumen of the body and not a body wall. For example, an operator may wish to confirm that the tool is within is within the stomach or other body organ. The tool need not be inserted into tissue. Thus, in such examples, the operator may not perform step 404, but proceed to step 406.

Figure 3:
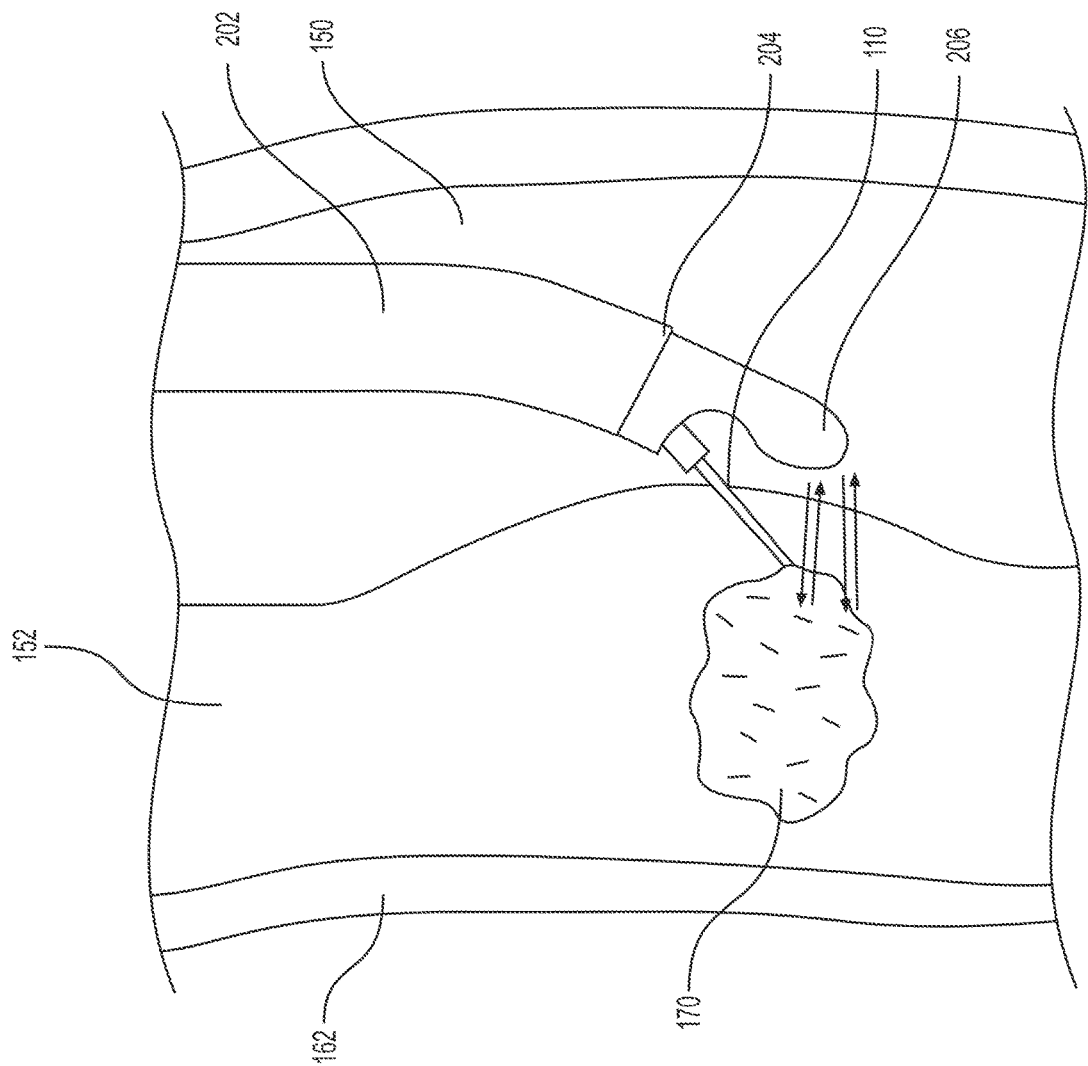
FIG. 3 illustrates an alternative, exemplary delivery device including a transducer and a tool injecting material into a patient's LES.

In an alternative exemplary embodiment, the delivery device may include a means of detecting, capturing, etc. the characteristics of the injected first material 170 instead of using an external device (e.g., an ultrasound device exterior of the patient). For example, an imaging device, ultrasound, transducer, etc. may be disposed on a surface of the delivery device or through a working channel of the delivery device. In another example, as shown in FIG. 3, the imaging device may be embedded in or near the distal end of the delivery device. Delivery device 202 includes a distal end 204 and an ultrasound transducer 206 integrally or detachable connected to distal end 204. Delivery device 202 may be utilized to perform method 400 as described above. For example, upon completion of step 406, injecting the first material, the transducer 206 (e.g., internal the patient and attached to delivery device 202) measures and/or observes at least one characteristic of the first material 170.

Embodiments of the present disclosure may be used in any medical procedure, including any medical procedure where precise positioning of a tool is desired. In addition, at least certain aspects of the above-mentioned embodiments may be combined with other aspects of the embodiments, or removed, without departing from the scope of the disclosure.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method of determining a position of a medical instrument, comprising:
   inserting the medical instrument into a body;
   inserting a first, fluidic material into the body and adjacent to the medical instrument;
   analyzing movement of the inserted first, fluidic material to be below a threshold value; and
   determining that the position of the medical instrument is within a desired region based on the analysis of the movement.

2. The method of claim 1, wherein the first, fluidic material includes a reflective material.

3. The method of claim 2, wherein the reflective material is at least one of zinc, aluminum, gold, silver, platinum, and gas bubbles.

4. The method of claim 2, wherein the first, fluidic material further includes water or saline.

5. The method of claim 1, further comprising:
   performing a medical procedure.

6. The method of claim 5, wherein the medical procedure includes injecting a second material.

7. The method of claim 6, wherein the second material is a bulking agent.

8. The method of claim 1, wherein the desired region is a lower esophageal sphincter.

9. The method of claim 8, wherein, after the position of the medical instrument is determined to be within the lower esophageal sphincter, the medical procedure further includes injecting a bulking agent into the lower esophageal sphincter.

10. The method of claim 1, wherein the analyzing step is a second analyzing step, and wherein the determining step is a second determining step, the method further comprising
    a first analyzing step that includes first analyzing the movement of the inserted first, fluidic material to be above a threshold value; and
    a first determining step that includes first determining that the position of the medical instrument is within a blood vessel, wherein the second analyzing step and the second determining step are performed after the first analyzing step and the second determining step.

11. The method of claim 10, further comprising:
    after the second determining step, repositioning the medical instrument, wherein the second analyzing step and the second determining step are performed after the repositioning step.

12. The method of claim 1, wherein the medical instrument is used to inject the first, fluidic material into the body.

13. The method of claim 1, wherein the analyzing step includes using an ultrasound device.

14. The method of claim 13, wherein the ultrasound device is disposed on the medical instrument.

15. The method of claim 1, wherein the first, fluidic material includes gas bubbles.

16. The method of claim 1, wherein the first, fluidic material includes a hypo-echoic fluid.

* * * * *